US009702801B2

(12) United States Patent
Etyemezian et al.

(10) Patent No.: US 9,702,801 B2
(45) Date of Patent: Jul. 11, 2017

(54) SYSTEM, APPARATUS, AND METHOD FOR MEASURING SURFACE MATERIALS

(71) Applicants: Vicken Etyemezian, Henderson, NV (US); George Nikolich, Las Vegas, NV (US)

(72) Inventors: Vicken Etyemezian, Henderson, NV (US); George Nikolich, Las Vegas, NV (US)

(73) Assignee: Board of Regents of the Nevada System of Higher Education on Behalf of the Desert Research Institute, Reno, NV (US)

( * ) Notice: Subject to any disclaimer, the term of this patent is extended or adjusted under 35 U.S.C. 154(b) by 245 days.

(21) Appl. No.: 14/316,276

(22) Filed: Jun. 26, 2014

(65) Prior Publication Data

US 2015/0000375 A1  Jan. 1, 2015

Related U.S. Application Data

(60) Provisional application No. 61/840,261, filed on Jun. 27, 2013.

(51) Int. Cl.
| | |
|---|---|
| *G01N 15/06* | (2006.01) |
| *G01N 15/02* | (2006.01) |
| *G01N 1/10* | (2006.01) |
| *G01N 15/00* | (2006.01) |
| *G01N 1/02* | (2006.01) |

(52) U.S. Cl.
CPC ............. *G01N 15/02* (2013.01); *G01N 15/06* (2013.01); *G01N 2001/028* (2013.01); *G01N 2001/1018* (2013.01); *G01N 2015/0046* (2013.01)

(58) Field of Classification Search
CPC .................. G01N 15/02; G01N 15/06; G01N 2015/0046; G01N 2001/028; G01N 2001/021; G01N 2001/1006; G01N 2001/1012; G01N 2001/1018; G01N 1/14; G01N 1/2273
See application file for complete search history.

(56) References Cited

U.S. PATENT DOCUMENTS

| | | | | |
|---|---|---|---|---|
| 4,932,705 | A * | 6/1990 | Miller | ................ B62D 33/0273 296/180.1 |
| 6,338,428 | B1 * | 1/2002 | Kawasaki | ................. B60R 9/04 224/309 |
| 2009/0026797 | A1 * | 1/2009 | Wood | ................... B62D 35/001 296/180.1 |

OTHER PUBLICATIONS

Article titled "Monitoring of dust emission on gravel roads" by Edvardsson et al. published in 2009.*
YouTube video titled "ProTech Aluminum Flatbed/Contractor Style Truck Bed At The NTEA Work Truck Show" published on Mar. 9, 2013.*
Etyemezian et al., "Measurement of Road Dust Emissions: The TRAKER and PI-SWERL Tools", Poster presented at *2008 Road Dust Management Practices and Future Needs Conference*, San Antonio, Texas, Nov. 13-14, 2008 (2008).

(Continued)

*Primary Examiner* — Blake A Tankersley
(74) *Attorney, Agent, or Firm* — Karquist Sparkman, LLP

(57) ABSTRACT

In one embodiment, the present disclosure provides a particulate monitoring system. The system includes a vehicle. A wake conditioner is mounted in the vehicle. A sample inlet is placed in communication with an engineered vehicle wake that will be produced by the wake conditioner when the vehicle is in motion.

20 Claims, 3 Drawing Sheets

(56) References Cited

OTHER PUBLICATIONS

Etyemezian et al., "Precision and Repeatability of the TRAKER Vehicle-Based Paved Road Dust Emission Measurement", *Atmospheric Environment* 40, 2953-2958 (2006).

Etyemezian et al., "TRAKER: A Method for Fast Assembly and Update of Paved and Unpaved Road Dust Emission Inventories", 27 pages, Presented at *14th International Emission Inventory Conference: Transforming Emission Inventories—Meeting Future Challenges Today*. Las Vegas, Nevada, Apr. 11-14, 2005 (2005).

Etyemezian et al., "Spatially-Resolved, Direct Measurement of Dust Emissions from Vehicles," 7th International Symposium on Urban and Highway Pollution, Barcelona, Spain, May 20-23, 2002, 39 pages.

Etyemezian et al., "Treasure Valley Road Dust Study: Final Report", *Desert Research Institute*, Prepared for the *Idaho Department of Environmental Quality*, Feb. 25, 2002, 200 pages (2002).

Etyemezian et al., "Vehicle-Based Road Dust Emission Measurement (I): Methods and Calibration", *Atmospheric Environment* 37, 4559-4571 (2003).

Etyemezian et al., "Vehicle-Based Road Dust Emission Measurement (III): Effect of Speed, Traffic Volume, Location and Season on PM10 Road Dust Emissions in the Treasure Valley, ID", *Atmospheric Environment* 37, 4583-4593 (2003).

Fackrell, J.E., "Parameters Characterising Dispersion in the Near Wake of Buildings", *Journal of Wind Engineering and Industrial Aerodynamics*, 16, 97-118 (1984).

Fitz, Dennis R., "Measurements of PM10 and PM2.5 Emission Factors From Paved Roads in California", Prepared for the *California Air Resources Board*, Jun. 2001. 70 pages., 70 pages (2001).

Fitz et al., "Measurement of PM10 Emission Rates from Roadways in Las Vegas, Nevada Using a SCAMPER Mobile Platform with Real Time Sensors", Presented at *14th International Emission Inventory Conference: Transforming Emission Inventories—Meeting Future Challenges Today*. Las Vegas, Nevada, Apr. 11-14, 2005, 24 pages (2005).

Gillies et al., "Characterizing and Quantifying Local and Regional Particulate Matter Emissions from Department of Defense Installations", Report Prepared for the *Strategic Environmental Research and Development Program*, Mar. 3, 2005. 102 Pages (2005).

Gillies et al., "Particulate Matter Emissions Factors for Dust from Unique Military Activities", Report Prepared for the *Strategic Environmental Research and Development Program*, Jun. 2010. 166 pages (2010).

Gomes et al., "Wind Tunnel Investigation on the Retention of Air Pollutants in Three-Dimensional Recirculation Zones in Urban Areas", *Atmospheric Environment* 41, 4949-4961 (2007).

Hajra et al., "The Effect of Upstream Buildings on Near-Field Pollutant Dispersion in the Built Environment", *Atmospheric Environment* 45, 4930-4940 (2011).

Humphries et al., "The Transport of Airborne Dusts in the Near Wakes of Bluff Bodies", *Chemical Engineering Science*, vol. 33, 1141-1146 (1978).

Kavouras et al., "Particle Dust Emission Factors from Unpaved Roads in the U.S.-Mexico Border Semi-Arid Region", *Journal of Arid Environments* 124, 189-192 (2016).

Kuhns et al., "Measurement and Modeling of Fugitive Dust Emissions from Paved Road Travel in the Lake Tahoe Basin", Report prepared for *USEPA Region 9*, San Francisco, California Dec. 31, 2007, 128 pages (2007).

Kuhns et al., "Spatial Variability of Unpaved Road Dust PM10 Emission Factors Near El Paso, Texas", *Journal of the Air & Waste Management Association*, vol. 55, 3-12 (2005).

Kuhns et al., "Testing Re-entrained Aerosol Kinetic Emissions from Roads (TRAKER): A New Approach to Infer Silt Loading on Roadways", *Atmospheric Environment* 35, 2815-2825 (2001).

Kuhns et al., "Vehicle-Based Road Dust Emission Measurement (II): Effect of Precipitation, Wintertime Road Sanding and Street Sweepers on Inferred PM10 Emission Potentials from Paved and Unpaved Roads", *Atmospheric Environment* 37, 4573-4582 (2003).

Langston, Rodney, "Mobile Sampling Methodology as an Alternative to Traditional AP-42 Silt Measurements", Presented at the *15th International Emission Inventory Conference: Reinventing Inventories—New Ideas in New Orleans*. New Orleans, Louisiana, May 15-18, 2006, 24 pages (2006).

Langston et al., "The Preferred Alternative Method for Measuring Paved Road Dust Emissions for Emissions Inventories: Mobile Technologies vs. The Traditional AP-42 Methodology", *Prepared for EPA OAQPS*, Mar. 2008, 84 pages.

"Other Test Method—34: Method to Quantify Road Dust Particulate Matter Emissions (PM10 and/or PM2.5) from Vehicular Travel on Paved and Unpaved Roads", 45 pages (2014) available at: http://www3.epa.gov/ttn/emc/prelim.html.

Teng et al., "Investigation of the AP-42 Sampling Method", *Journal of the Air & Waste Management Association*, vol. 58, pp. 1422-1433 (2008).

Vincent, J.H., "Model Experiments on the Nature of Air Pollution Transport Near Buildings", *Atmospheric Environment* vol. II., 165-774 (1977).

Watson et al., "Overview of Real-World Emission Characterization Methods", *Developments in Environmental Science*, vol. 11. pp. 145-170 (2012).

Zhu et al., "Analysis of the Effectiveness of Control Measures to Mitigate Road Dust Emissions in a Regional Network", *Transportation Research Part D* 17, 332-340 (2012).

Zhu et al., "Fugitive Dust Emissions from Paved Road Travel in the Lake Tahoe Basin", *Journal of the Air & Waste Management Association*, vol. 59, 1219-1229 (2009).

\* cited by examiner

SYSTEM, APPARATUS, AND METHOD FOR MEASURING SURFACE MATERIALS

CROSS REFERENCE TO RELATED APPLICATION

This application claims the benefit of, and incorporates by reference, Provisional Patent Application Ser. No. 61/840,261, filed Jun. 27, 2013.

FIELD

The present disclosure relates generally to monitoring particulates. In a specific example, the present disclosure provides a system for monitoring particulates taken from an engineered vehicle wake formed by a wake conditioner.

SUMMARY

Certain aspects of the present disclosure are described in the appended claims. There are additional features and advantages of the various embodiments of the present disclosure. They will become evident from the following disclosure.

In this regard, it is to be understood that the claims form a brief summary of the various embodiments described herein. Any given embodiment of the present disclosure need not provide all features noted above, nor must it solve all problems or address all issues in the prior art noted above or elsewhere in this disclosure.

BRIEF DESCRIPTION OF THE DRAWINGS

Various embodiments are shown and described in connection with the following drawings in which.

DETAILED DESCRIPTION

Figure 1:
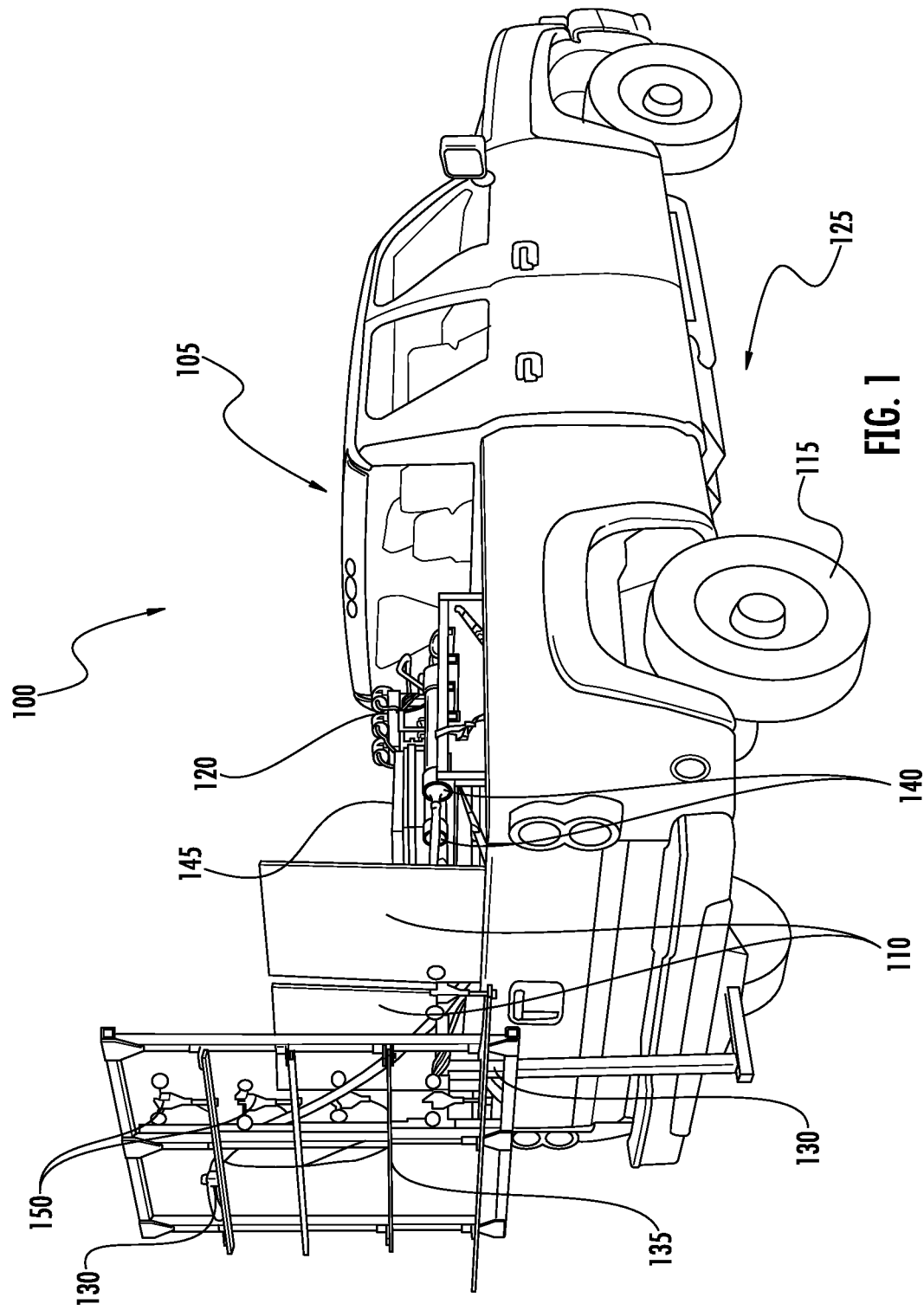
FIG. 1 is a photograph of a particulate monitoring system according to an embodiment of the present disclosure.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together. Although methods and materials similar or equivalent to those described herein can be used in the practice or testing of the present disclosure, suitable methods and materials are described herein. The disclosed materials, methods, and examples are illustrative only and not intended to be limiting.

In one embodiment, the present disclosure provides a mobile monitoring system for measuring, collecting, or characterizing materials from surfaces of interest. Unlike other sampling systems, the disclosed system does not require an inlet tube behind the tire(s) of the test vehicle to sample materials suspended from roads. The disclosed system also does not require an inlet tube to be placed at considerable distance behind the test vehicle to accurately measure/collect/characterize suspendable materials. Instead, aerodynamic modification of the test vehicle allows for accurate measurement/collection/characterization of suspendable materials in close proximity behind the test vehicle in the engineered wake. Among other advantages, the disclosed system can allow a larger range of vehicles to be used obtain measurements, as the system can be more easily retrofit into existing vehicles.

In one implementation, the disclosed system includes a vehicle and wake conditioner, such as a baffle, suitably mounted in the vehicle to produce an engineered vehicle wake when the vehicle is placed in motion. The system further includes a sample inlet and a sample collection and/or sample analysis unit.

The wake conditioner may be made from a variety of materials, including wood, metal, plastics, composites, and combinations thereof. The wake conditioner can also be formed in a variety of shapes, including circles, squares, rectangles, ovals or other shapes. The wake conditioner can be a flat surface, or can have curved or bent portions, including as described below, which can help influence the size of the engineered vehicle wake and the wake's interaction with the surrounding environment.

The wake conditioner is typically sized to provide an engineered vehicle wake of a desired size and stability. In general, the size of the wake conditioner as viewed from the direction of travel of the vehicle determines the size of the engineered vehicle wake. In some implementations, such as when the wake conditioner is a baffle, the wake conditioner performs its function by causing a sharp pressure drop in its lee. Consequently, air from around the perimeter of the wake conditioner is sucked into its lee side and mixed through the action of wake turbulence. In order to entrain particles that are suspended by the movement of the vehicle, such as the action of vehicle tires on a surface, it is useful, in specific implementations, for the wake conditioner to be at least as wide as the vehicle's wheelbase (when the vehicle is a wheeled vehicle). In this manner, particles entrained by tires on both left and right side of the vehicle are sucked into the engineered vehicle wake.

In another implementation, the wake conditioner is wide enough to span only half the width of the vehicle and positioned to sample only either the left or right sides of the vehicle for particles. In yet another implementation, the wake conditioner is wider than the sides or wheelbase of the vehicle. This may be useful, for example, when relatively small vehicles are to be used or when a larger engineered vehicle wake is otherwise desired. A wider wake conditioner can also be useful in helping to ensure that more particulates that are disturbed as a result of vehicle movement are pulled in to the engineered vehicle wake so that they can be measured or analyzed.

The wake conditioner is typically positioned in close proximity to the vehicle's rear, such as the rear bumper of a car or truck, to help ensure that particle laden air that is being channeled underneath the vehicle is directed into the engineered vehicle wake. If there is a substantial gap between the bottom of the wake conditioner and the rearmost vertical surface of the vehicle (bumper or equivalent), then it is possible that the air sucked in at the bottom and lee side of the baffle would originate from elsewhere, such as the side of the vehicle.

As described above, at least certain wake conditioners act by introducing a sharp pressure drop in its lee. However, this sharp pressure drop can also result in undesirable vortex shedding at the edges of the wake conditioner and at the termination of the engineered vehicle wake behind the vehicle. This vortex shedding can have the effect of introducing air from aloft into the engineered vehicle wake and mixing it with the dust laden air in an inconsistent and potentially undesirable fashion. Additionally, vortex shedding may result in the intermittent collapse of the engineered vehicle wake.

In one embodiment of the present disclosure, this effect is ameliorated by using a wake conditioner with rounded edges, including edges bent towards the lee of the wake conditioner. Compared with a sharp-edged, flat wake conditioner, this has the effect of dulling the pressure drop behind the wake conditioner and maintaining the fluid stream lines. In another embodiment of the present disclosure, this effect is ameliorated by making the wake conditioner porous in some regions along the perimeter of the wake conditioner or throughout the entire surface of the wake conditioner. Allowing a small aliquot of air to flow through the pores has the effect of conditioning the otherwise sharp pressure drops and buffering the aerodynamic instability that results from a solid, flat wake conditioner.

The sample inlet is placed in the engineered vehicle wake or placed in communication with the engineered vehicle wake. For example, a conduit, such as a tube, can be placed in communication with the engineered vehicle wake, such as by being suitably mounted to the vehicle, and coupled to the sample inlet.

The engineered vehicle wake is typically well mixed and fairly consistent/homogenous. In a specific implementation, "at least substantially consistent" or "at least substantially homogenous" means that concentration (or other data) obtained at a plurality of locations have correlation coefficients of at least about 0.80, such as at least about 0.85, such as at least about 0.90. In particular example, the correlation coefficient exceeds at least about 0.95. The measured parameter at each location need not be exactly the same, so long as the values are highly correlated. For example, the values may be proportional to one another, such as having proportionality constants of about 15 or less, such as about 10 or less, such as about 5 or less. In a specific example, the proportionality constant is about 2 or less.

In some embodiments, data obtained using a system according to an embodiment of the present disclosure, or a using a method according to an embodiment of the present disclosure, can be compared to data obtained using other measurement techniques or converted to a standard. In a particular example, data obtained under the present disclosure can be related to other data through the use of a multiplier or other mathematical relationship.

Small deviations in the wind speed, wind direction, vehicle travel speed, or location of the sample inlet (such as by vibration) do not typically result in measurable differences in particle concentration/characteristics. Advantageously, the engineered vehicle wake is typically substantially independent of vehicle speed once the net wind speed exceeds that required for Reynold's number independence (such as Re>100,000). The profiling technique can be used to empirically identify the region within the wake where the sample concentration is essentially location independent. Thus, it is possible obtain accurate and precise samples so long as the sample received by the sample inlet comes from the engineered vehicle wake.

The engineered vehicle wake typically begins at a certain distance from the wake conditioner, such as any area of inhomogeneity caused by the vehicle, such as suction resulting from the underside of the vehicle, to a second distance where the effect of the wake conditioner starts to wear off. In some examples, the engineered vehicle wake extends from several centimeters, such as at least about 10 centimeters, beyond the wake conditioner, to a distance from the wake conditioner equal to about three times the height of the wake conditioner. Areas of the engineered vehicle wake further from the wake conditioner typically have pressure forces that maintain the wake which are not as large as those at closer distances. Thus, the wake bubble in this more remote region can meander in response to cross winds or collapse periodically in response to turbulent forcing.

The size and stability of the engineered vehicle wake may be influenced by the size and shape of the wake conditioner. The nature of the engineered vehicle wake in relation to a particular wake conditioner can be empirically determined. However, generally, vehicles are designed to be aerodynamically streamlined to minimize wind (or other fluid) resistance. An engineered vehicle wake is made possible by introducing a sudden interruption in the flow of air over the vehicle by means of a wake conditioner (such as a baffle, block, series of trip wires, fence, etc). The effect of the wake conditioner is to reduce the pressure immediately behind the rear of the vehicle and effectively suction the particle-laden air that is passing underneath the vehicle and to some degree along the sides of the vehicle. This particle laden air has been injected with particles (in the case of suitable land vehicle) by the rolling action of the tires.

The shape of the engineered vehicle wake is approximately half an ovaloid, with the tapered end pointing way from the wake conditioner. Immediately behind the wake conditioner, the shape of the engineered vehicle wake is generally similar to the shape of the wake conditioner. Over a distance equal to about 4-10 wake conditioner heights (depending on the specific shape of the water conditioner), the size/shape of the wake tapers back to a point. The size of the wake is generally speed independent when the Reynolds number exceeds 100,000. As a specific example, for a 1.5 meter X 1.5 meter wake conditioner, speed independence is approximately achieved at net vehicle speeds over approximately 2 meters per second or 4 miles per hour.

As described above, the nature of the engineered vehicle wake can empirically determined or modeled. In a particular example, the engineered vehicle wake can be empirically determined by taking samples from behind the center of the wake conditioner while also taking samples from various locations around and distances from the wake conditioner. A measured portion of the wake may be considered part of the engineered vehicle wake if the measured value is sufficiently correlated with the value measured at the center (reference) point, as described above.

In specific implementations, the system can further include a pump. The pump may be palette-mounted, which can facilitate transferring components of the system to another vehicle. Some implementations do not include a pump, such as passive sampling systems. In one passive sampling system, particles are collected on a sticky surface. In a method using passive sampling, the difference in the weight of a sample collection device (such as a sticky surface) before and after sample acquisition is used to gain information about the particles collected during sampling, such as suspendible particles created by vehicle motion. The collected samples may be further analyzed, such as using a microscope or by chemical analysis.

In another example of passive sampling, pressure differences in the engineered vehicle wake created by the wake conditioner can be used to drive airflow into a sample collector or sample analyzer.

In another specific implementation, the system further includes a power source. The power source can be used, for example, to power a pump or sample analysis instruments. In a specific example, the power source is part of the vehicle, such as being connected to the vehicle's battery/electrical system. In another example, the system includes its own power source, such as a generator or battery. In yet another example, the system does not require power.

In at least some embodiments, the system includes instruments for analyzing/quantifying materials collected from the engineered vehicle wake. This can be in addition to or in place of collecting (and storing) a portion of the sample for later reference. By way of example, the instruments can include those to measure the quantity/concentration of particles, the size/size distribution of particles, the weight/weight distribution of particles, and instruments to identify the nature of the particles, including spectroscopic measurements or chemical analysis. More specific examples of instruments that can be part of the disclosed system include devices to measure PM mass concentration, such as the TSI DUSTTRACK, and the GRIMM Particle Size Analyzer. An example of specific instruments that can be included in the present disclosure, as well as methods of using them, can be found, in Etyemezian, et al., "Vehicle-based Road Dust Emission Measurement: I-Methods and Calibration," *Atmospheric Environment* 37:4559-4571 (2003), incorporated by reference herein in its entirety.

The system can include additional components, such as a manifold, to distribute portions of the sample to multiple instruments/collectors. The system can also include components to condition the sample, such as filters, size selectors, or diluters (such as when a sample may be too concentrated to feed directly into a particular instrument).

The system may also include a controller, such as a computer. The controller may be used, for example, to control and monitor operation of other system components, such as the pump, sample analyzers, and environmental monitors (temperature and pressure gauges, wind speed/direction measurements, location measurements, etc). The controller may also perform data recording and processing functions. In specific embodiments, the controller is configured to transmit data to a remote location in real time.

These components are placed in a suitable vehicle. In a specific example, the vehicle is a pickup truck and the components are placed in the bed of a pickup truck. A sampling line is run past the back of the vehicle.

A baffle is placed at the back of the vehicle. The baffle is suitably dimensioned and constructed to produce a desired amount of turbulence to the air in the vehicle's wake. In a specific example, useable when the system is used with a standard American pick up truck, the baffle has dimensions of about 1.5 meters by 1.5 meters. The baffle can be secured to the vehicle through appropriate means.

The baffle acts to condition and homogenize the aerodynamic wake behind the vehicle. As the test vehicle travels, material that is suspended from a surface, such as a road, either by interaction with the vehicle tires or by aerodynamic forces exerted by the vehicle, is lifted into the vehicle's modified wake bubble, where it is mixed by the action of turbulence in the engineered vehicle wake. A sample of this material is acquired through the sample line. In some cases, the sample may be saved for later analysis. In other cases, the sample may be analyzed, as for its concentration, chemical properties, or physical properties in-situ. In yet further cases, some measurements may be made in situ with the sample being also preserved for later use of analysis. In the case of particulate matter from road dust measurement, the dust-laden air is sampled into a sampling plenum and analyzed by optical instruments or collected on sampling media for subsequent analysis.

In particular embodiments, the method of the present disclosure can measure quantities in addition to particle properties. For example, wind speed can be measured, such as using an anemometer, along with wind direction, such as using a wind vane, in order to accomplish wind profiling. Wind profiling can help ensure that the vector-averaged wind direction is within +/−30 degrees of the vector pointing in the direction of the rear of the vehicle. That is, the engineered vehicle wake is improved when the direction and magnitude of the ambient wind are such that from the perspective of the vehicle the net wind speed is 5 meters per second or higher and the net wind direction is from 150-210 degrees from the direction of travel of the vehicle. If the speed of the vehicle is less than the speed of the wind, the wake conditioner may not be effective. Similarly, the wake conditioner may not be effective if the cross winds are too high. In some cases, the vehicle speed can be increased in order to help produce and sustain a desired engineered vehicle wake given higher cross winds or less than ideal wind direction.

In another embodiment, position information, such as GPS coordinates, and related quantities such as ground speed, travel direction, acceleration/deceleration, and rate of turn are recorded/measured. These quantities can be used, for example, to screen data. For example, data obtained during periods of high acceleration might be selected and excluded from use if suspension at cruising speeds was of primary interest.

Another quantity that can be measured is pressure within the sample lines. Pressure within the sample line can be used as an indicator of whether or not there may be leaks or blockages in the sampling lines. Similarly, the sample flow rate through the sampling line is metered or measured in some embodiments to ensure that it is within an acceptable range. Some instruments that may be used to analyze the sample from the sample inlet require very specific sample flows. For example, sampling for particles of a certain size (for example, less than 10 microns) in some cases requires that the sample flow through a specially designed inlet at a specified flow rate.

Another reason for measuring sample flow is that it can be desirable to minimize the amount of time between when a sample is procured at the inlet and when it is presented to real-time instruments. That is, in some setups, higher flow rates tend to reduce sample retention time. Yet another reason for measuring sample flow rates is that, when sampling particles, high flow speeds through sample lines can sometimes result in undesirable inertial removal of particles, especially near corners and bends in the sample line. Flow measurements can be used to optimize flow rates to minimize the delay between sampling and measurements while also minimizing inertial removal of particles.

Air temperature and barometric (outside) pressure are also measured, in some implementations, to assist in referencing the particle or other concentration to sea level—as is desirable under certain reporting requirements (such as for the EPA).

FIG. 1 is a photograph of an example system 100 according to an embodiment of the present disclosure. The system 100 includes a vehicle 105, a pickup truck. A vehicle wake conditioner 110, in the form of a plywood baffle (being split down the middle in order to accommodate mounting hardware), is mounted in the back of the vehicle 105.

The vehicle 105 includes tires 115 that cause particulate matter, such as dust, from a surface 125 to become suspended as the vehicle 105 travels over the surface 125. Tubing 130 is supported at the back of the vehicle 105 by mounting brackets 135. The tubing 130 is connected to respective sample inlets 140. The sample inlets 140, and thus tubing 130, are coupled to analysis instruments 145 and a pump 120. Anemometers 150 are coupled to the mounting brackets 135.

In operation, the vehicle 105 drives over the surface 125, causing dust and other particles to be suspended under and behind the vehicle 105. Some of this particulate matter enters an engineered vehicle wake behind the vehicle 105 created by the wake conditioner 110. A sample of the wake is pulled through the tubing 130 and the sample inlet 140 by the pump 120. The sample obtained is analyzed using instruments 145. Wind conditions around the vehicle are monitored by anemometers 150.

Figure 2:
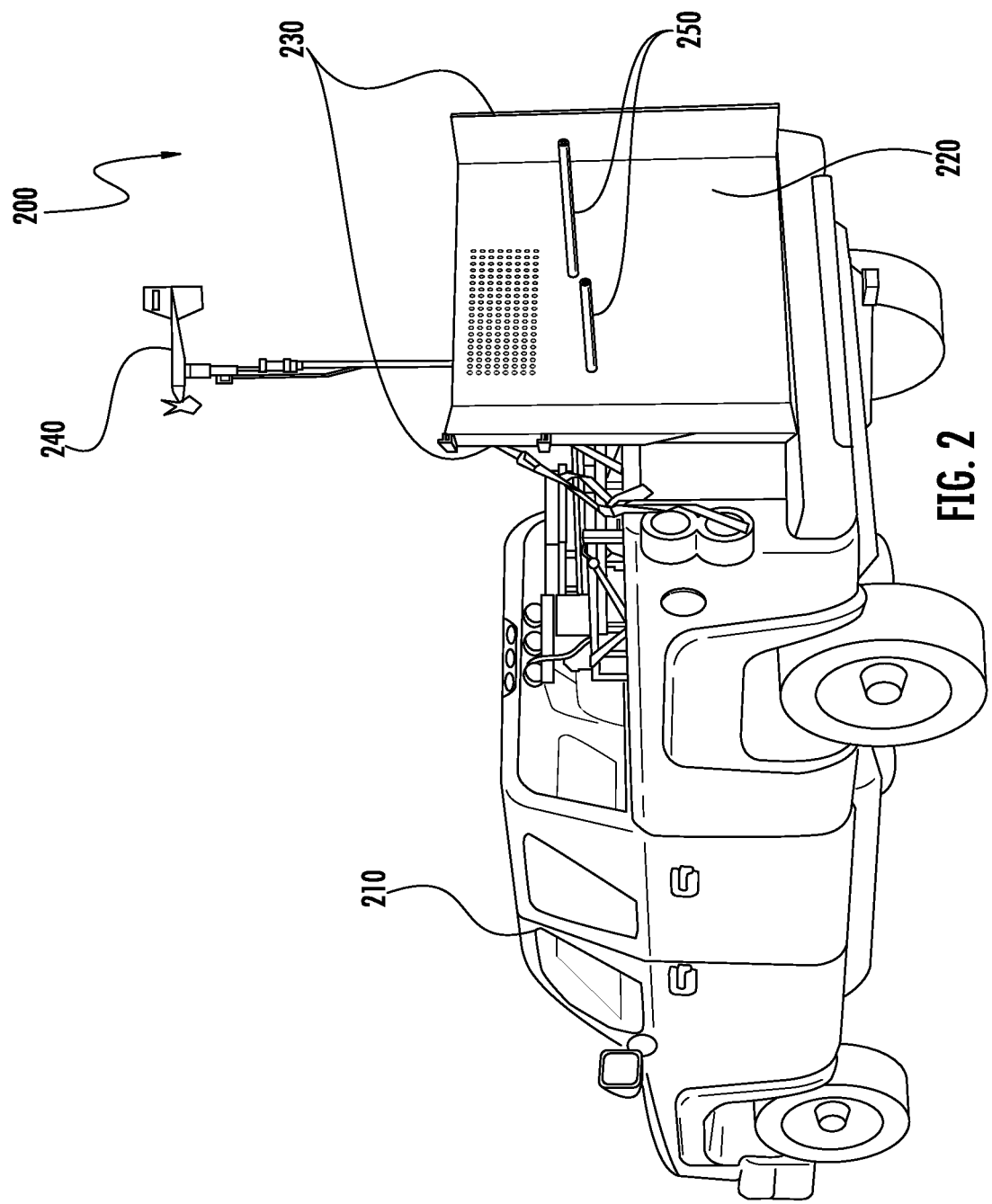
FIG. 2 is a photograph of a particulate monitoring system according to an embodiment of the present disclosure.

FIG. 2 is a photograph of monitoring system 200 according to an embodiment of the present disclosure. The system 200 is generally similar to the system 100 of FIG. 1. A baffle 220 is mounted to a vehicle 210. The baffle 220 is made of perforated metal. The baffle 220 includes sides 230 which are angled back from the end of the vehicle 210. As described above, this can serve to reduce the pressure drop caused by the baffle 220. The system 200 includes a wind vane 240, which can be used to aid in profiling winds during sample acquisition. Conduits 250 penetrate the baffle 220 for obtaining a sample to be carried to sample inlets by a pump (not shown, but analogous to FIG. 1).

Figure 3:
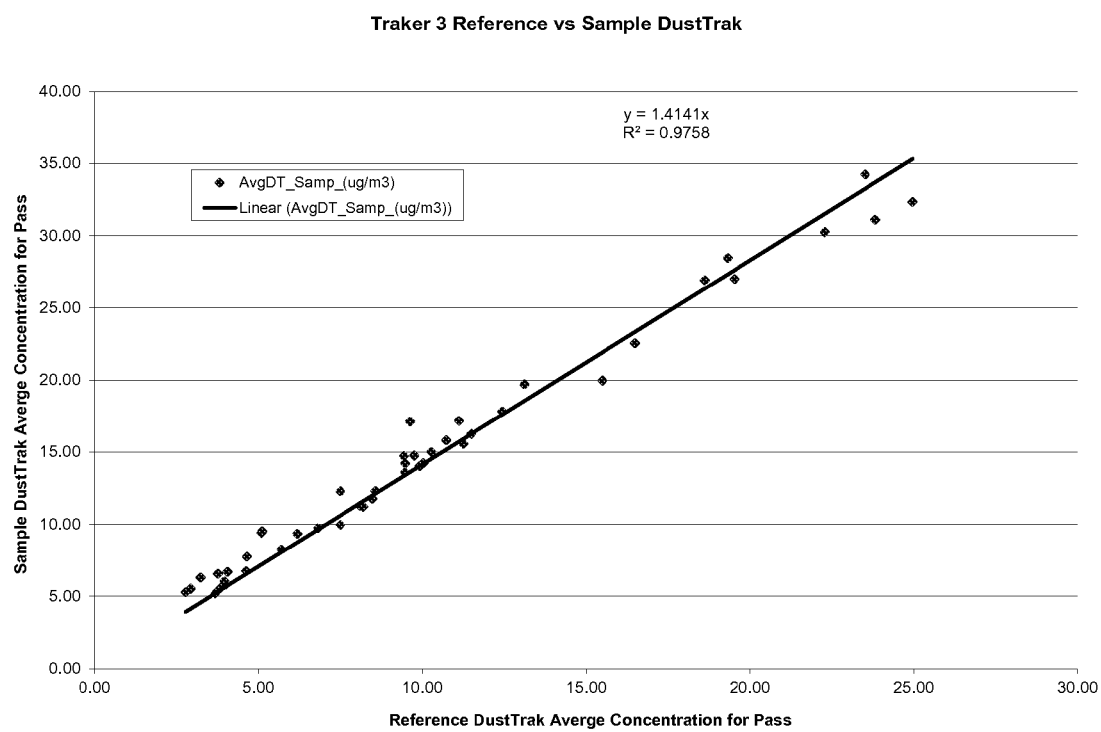
FIG. 3 is a graph of dust concentration data obtained using a system according to an embodiment of the present disclosure at two different locations within an engineered vehicle wake.

FIG. 3 is a graph of particle data obtained from two different points in the engineered vehicle wake produced using a system according to an embodiment of the present disclosure. The data shows excellent correlation. This indicates that the measurement in the wake is very stable and insensitive to location (as long as it remains within wake).

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

What is claimed is:

1. A particulate monitoring system comprising:
a vehicle comprising a front portion and a rear portion and defining a longitudinal axis, the rear portion defining two longitudinally extending lateral sides and a laterally extending end portion, the two longitudinally extending lateral sides and the laterally extending end portion each having a height, the heights of the two longitudinally extending lateral sides and the laterally extending end portion being at least substantially the same;
a wake conditioner comprising a forward face and a rearward face, the forward and rearward faces defined by a length and a width of the wake conditioner, the wake conditioner mounted proximate the rear portion of the vehicle such that the forward and rearward faces are perpendicular to the longitudinal axis of the vehicle, wherein the wake conditioner extends above an upper surface of the laterally extending end portion of the rear portion of the vehicle; and
a sample inlet disposed rearwardly of the rearward surface of the wake conditioner, wherein the wake conditioner increases turbulence behind the rear portion of the vehicle, and produces an engineered vehicle wake behind the vehicle, when the vehicle is in motion and the sample inlet is in communication with the engineered vehicle wake and is configured to obtain a sample from the engineered vehicle wake.

2. The system of claim 1, further comprising a pump mounted to the vehicle and in communication with the sample inlet.

3. The system of claim 1, further comprising a sample collector in communication with the sample inlet.

4. The system of claim 1, further comprising a sample analyzer in communication with the sample inlet.

5. The system of claim 1, wherein the wake conditioner comprises a baffle.

6. The system of claim 1, wherein the wake conditioner is perforated, the perforations defining apertures for allowing the passage of fluid through the wake conditioner.

7. The system of claim 1, wherein the wake conditioner has rounded edges.

8. The system of claim 1, wherein the wake conditioner has sides angled in a manner to reduce the pressure drop behind the wake conditioner.

9. The system of claim 1, further comprising a wind monitor.

10. The system of claim 1, further comprising a GPS tracker.

11. The system of claim 1, wherein the vehicle defines a track at the rear portion of the vehicle, the track having a width, the forward face of the wake conditioner being wider than the width of the track.

12. The system of claim 1, wherein the vehicle defines a width between the longitudinally extending lateral sides, the forward face of the wake conditioner being wider than the width between the longitudinally extending lateral sides.

13. The system of claim 1, wherein the vehicle defines a track at the rear portion of the vehicle, the track having a width, the forward face of the wake conditioner being at least as wide as the width of the track.

14. The system of claim 1, wherein the forward and rearward faces of the wake conditioner are flat.

15. The system of claim 1, wherein the forward and rearward faces are square.

16. The system of claim 1, wherein the wake conditioner is dimensioned to produce a wake having a Reynolds number exceeding 100,000 when the vehicle is in motion and exceeds a speed of about 4 miles per hour.

17. The system of claim 1, wherein the vehicle is a truck and the laterally extending end portion of the rear portion of the vehicle is a tailgate.

18. The system of claim 1, wherein the vehicle is a truck, the truck comprises a bed, the laterally extending end portion is a tailgate, and the wake conditioner is mounted to the bed.

19. A particulate monitoring system comprising:
a vehicle comprising a front portion, a rear portion, and defining a longitudinal axis, the rear portion defining two longitudinally extending lateral sides, each longitudinally extending lateral side having a height;
a wake conditioner comprising a front face and a rear face, the front and rear faces defined by a length and a width of the wake conditioner, the wake conditioner mounted proximate the rear portion of the vehicle such that the front and rear faces are perpendicular to the longitudinal axis of the vehicle and an upper surface of the wake conditioner extends above the heights of the longitudinally extending lateral sides of the rear portion of the vehicle, and configured to increase turbulence behind the rear portion of the vehicle, and produce an engineered vehicle wake behind the rear portion of the vehicle, when the vehicle is placed in motion;

a sample inlet in communication with the engineered vehicle wake;

a sample analyzer;

a pump;

tubing connecting the sample inlet, sample analyzer, and pump;

a wind monitor; and a controller coupled to the pump, the sample analyzer, and the wind monitor.

20. A particulate monitoring system comprising:

a vehicle comprising a front portion and a rear portion and defining a longitudinal axis, the rear portion defining two longitudinally extending lateral sides, the two longitudinally extending lateral sides each having a height;

a wake conditioner comprising a forward face and a rearward face, the forward and rearward faces defined by a length and a width of the wake conditioner, the wake conditioner mounted proximate the rear portion of the vehicle such that the forward and rearward faces are perpendicular to the longitudinal axis of the vehicle, wherein the wake conditioner extends above the heights of the longitudinally extending lateral sides of the rear portion of the vehicle; and a sample inlet disposed rearwardly of the rearward surface of the wake conditioner, wherein the wake conditioner increases turbulence behind the rear portion of the vehicle, and produces an engineered vehicle wake behind the vehicle, when the vehicle is in motion and the sample inlet is in communication with the engineered vehicle wake and is configured to obtain a sample from the engineered vehicle wake.

* * * * *